United States Patent

Kloster

(10) Patent No.: US 9,050,162 B2
(45) Date of Patent: Jun. 9, 2015

(54) BRUSHHEAD FOR A POWER TOOTHBRUSH WITH MOVING PADDLE MEMBERS

(71) Applicant: KONINKLIJKE PHILIPS N.V., Eindhoven (NL)

(72) Inventor: Tyler G. Kloster, Snoqualmie, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/366,311

(22) PCT Filed: Dec. 11, 2012

(86) PCT No.: PCT/IB2012/057165
§ 371 (c)(1),
(2) Date: Jun. 18, 2014

(87) PCT Pub. No.: WO2013/093709
PCT Pub. Date: Jun. 27, 2013

(65) Prior Publication Data
US 2014/0373291 A1    Dec. 25, 2014

Related U.S. Application Data

(60) Provisional application No. 61/578,961, filed on Dec. 22, 2011.

(51) Int. Cl.
*A61C 17/22*      (2006.01)
*A61C 17/34*      (2006.01)

(52) U.S. Cl.
CPC ........... *A61C 17/222* (2013.01); *A61C 17/3418* (2013.01); *A61C 17/3472* (2013.01)

(58) Field of Classification Search
CPC ......................... A61C 17/222; A61C 17/3472
USPC ........................................ 15/22.1, 22.2, 22.4
See application file for complete search history.

(56) References Cited

U.S. PATENT DOCUMENTS

| 5,842,249 | A | 12/1998 | Sato | |
| 6,760,946 | B2* | 7/2004 | DePuydt | 15/22.4 |
| 8,397,332 | B2* | 3/2013 | Kraus et al. | 15/22.1 |

FOREIGN PATENT DOCUMENTS

| DE | 202005011363 U1 | 9/2005 |
| WO | 2009148439 A1 | 12/2009 |

* cited by examiner

*Primary Examiner* — Randall Chin

(57) ABSTRACT

A power toothbrush brushhead includes a neck portion which is attachable to a drive member of the power toothbrush which operates in a sweeping, i.e. partially rotating, manner. The brushhead includes a neck portion and a bristle base member at a distal end of the neck portion. The bristle base member includes a central portion and two paddle members on opposing sides of the central portion. The central portion and paddle members are supported at one end thereof in cantilever fashion from the distal end of the neck portion, with the other ends thereof being free to move. The action of the drive member moves the central portion in a sweeping, back-and-forth, motion, which results in an in-and-out movement of the two paddle members.

6 Claims, 3 Drawing Sheets

BRUSHHEAD FOR A POWER TOOTHBRUSH WITH MOVING PADDLE MEMBERS

CROSS-REFERENCE TO PRIOR APPLICATIONS

This application is the U.S. National Phase application under 35 U.S.C. §371 of International Application No. PCT/IB2012/057165, filed on Dec. 11, 2012, which claims the benefit of U.S. Provisional Patent Application No. 61/578,961, filed on Dec. 22, 2011. These applications are hereby incorporated by reference herein.

This invention relates to power toothbrushes, and more specifically concerns a new brushhead for use with power toothbrushes.

Several power toothbrushes available from different manufacturers feature multiple-motion brushhead action. The separate motions vary, including for example a combination of rotary motion and longitudinal (back-and-forth) motion and/or in-and-out (toward and away from the teeth) motion. In addition, some power toothbrushes feature a brushhead moving in complex patterns, such as a figure eight. However, these multi-motion brushheads typically have at least two significant disadvantages. The brushheads use standard mechanical linkages, including cam-driven and gear-driven arrangements, to create the multiple motions. These mechanical linkages require a significant amount of space, which increases the size of the brushhead, as well as cost. In addition, such mechanical linkages which operate in an effective frequency range similar to that of sonic frequency toothbrushes (150-300 Hz) are typically quite noisy and usually experience excessive wear in a short time of operation. These mechanical linkages also are frequently complex in order to produce the desired multiple brushhead motions, and are therefore subject to short life and/or breakdown.

The present arrangement produces multiple brushhead motions effective in cleaning teeth at a resonant frequency without use of typical mechanical linkages and therefore overcomes the disadvantages of conventional multi-motion toothbrush heads.

Accordingly, the brushhead for use with a power toothbrush having a back-and-forth sweeping-type driving motion produced by a drive assembly comprises: a neck portion configured for attachment to an extending portion of the drive assembly; and a bristle base member positioned at a distal end of the neck portion, the bristle base member including a central portion and two paddle members on opposing sides of the central portion, the central portion and the paddle members extending in cantilever fashion, respectively, from the distal end of the neck portion, wherein opposing ends of the central portion and the paddle members are free to move, wherein the central portion follows the movement of the drive member in a back-and-forth sweeping motion for action along the teeth, while the two paddle members move in and out, toward and away from the teeth.

Figures 1, 2:
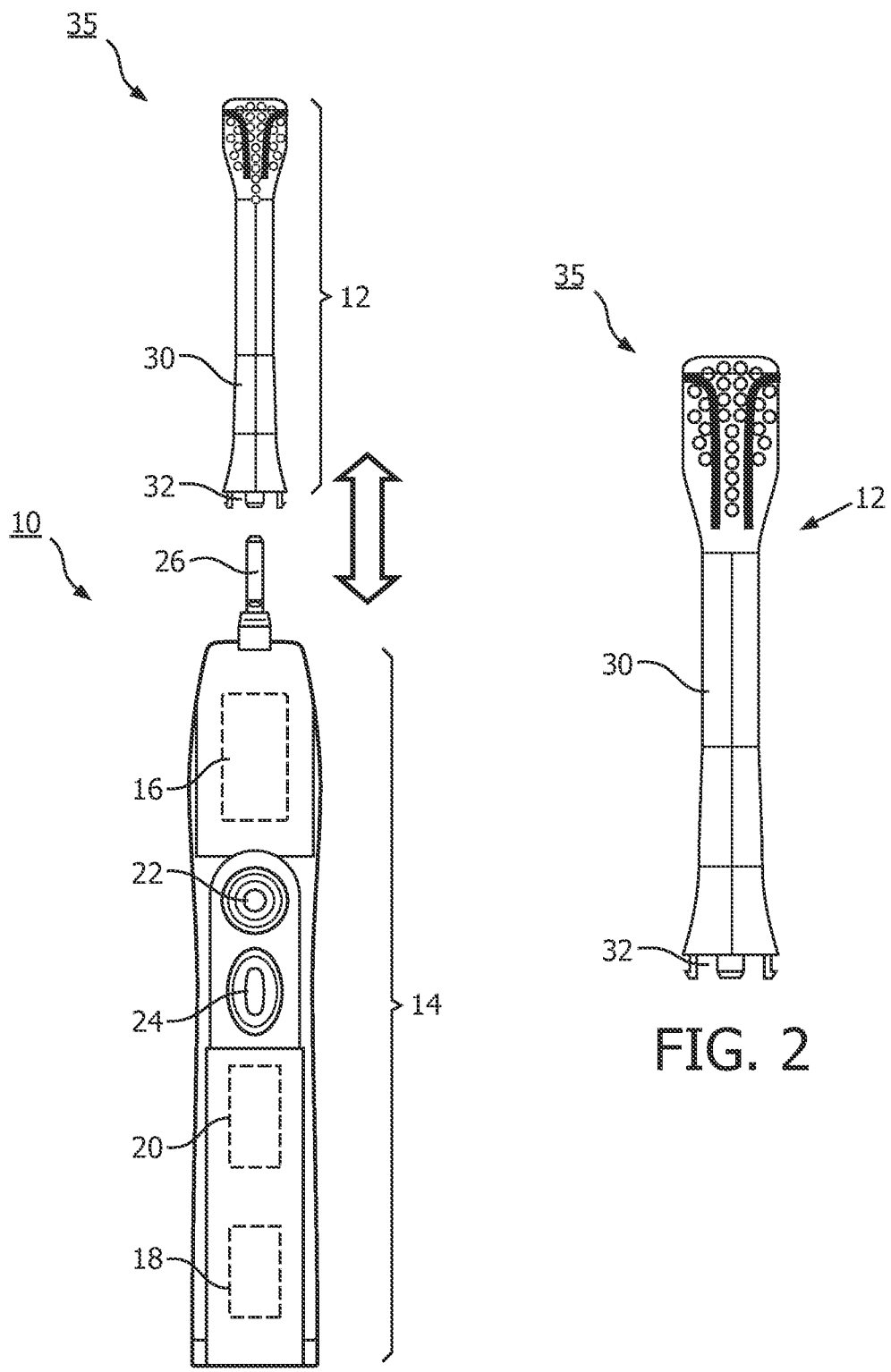
FIG. 1 is an elevational view of a power toothbrush with the brushhead of the present invention.
FIG. 2 is a top view of a brushhead embodying the present invention.

FIG. 1 shows a power toothbrush generally at 10 which includes the brushhead 12 of the present invention and a handle portion 14. Handle portion 14 in general includes a drive assembly 16 powered by a rechargeable battery 18 and controlled by a microprocessor 20. The handle also includes an on/off switch 22 and a control button 24 for controlling the mode of operation of a multi-mode toothbrush. The drive assembly 16 includes a driveshaft 26 which produces a sweeping (partial rotation) motion of the brushhead assembly 12. The rotational amplitude is 5-28°, with a preferred range of 7-14°. The proper operation of the present brushhead 12 requires such a sweeping, i.e. partial rotation, motion.

Figure 3:
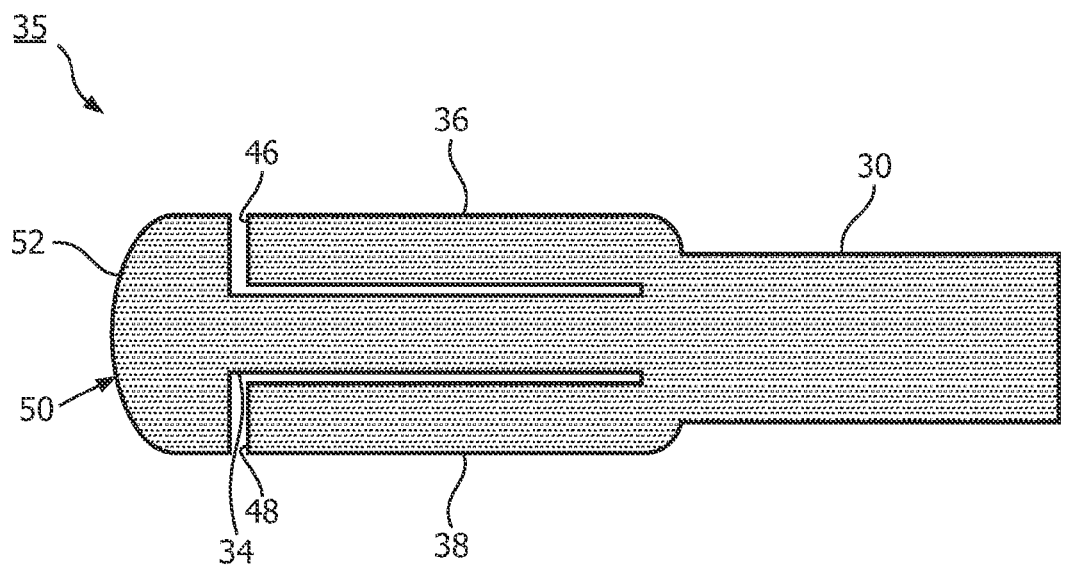
FIG. 3 is a top view of one embodiment of the bristle base portion of the new brushhead, without bristles.
Figure 5:
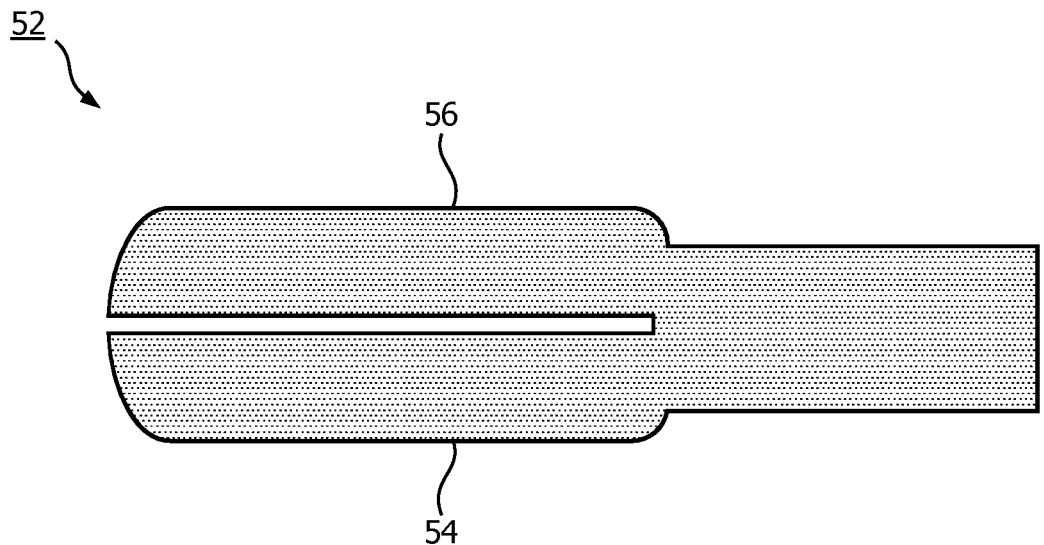
FIG. 5 is a top view of another embodiment of the bristle base portion, without bristles.

Brushhead 12 includes an elongated, slim neck portion 30 which is hollow at a proximal end 32, into which driveshaft 26 securely fits. At the distal end of neck portion 30 is a bristle base member 35 which is particularly configured and structured to produce a multi-motion action involving separate portions of the bristle base assembly and hence the bristles thereon, or alternatively, a single-motion action toward and away from the teeth of the user. The multi-motion arrangement, however, is preferred, and is illustrated in the brushhead of FIGS. 1, 2 and 3. The alternative motion arrangement is shown in FIG. 5.

Referring now to FIGS. 2 and 3, the bristle base member includes a central portion 34 and two side paddle member portions 36 and 38 on opposing sides of the central portion. In the embodiment shown, the overall width of the brushhead is 13 mm, although it could be smaller, while the width of the central portion is approximately 2-5 mm and the width of each of the two paddle member portions is also 2-5 mm. The central portion and the two paddle members are substantially co-planar, with the two paddle members being substantially identical. The central portion 34 and the two paddle members 36, 38 are connected at their proximal ends to the distal end of the brushhead neck portion. The opposing free ends 46, 48 of the two paddle members are free to move. In the embodiment shown in FIGS. 2 and 3, the central portion 34 extends beyond the free ends of the two paddle members 36, 38 and includes a cap-like end piece 50 which extends between the outer sides of the two paddle members and forward of the free ends thereof, terminating in a curved end surface 52. The central portion and the two paddle members can be integral with of the neck portion of the brushhead, or they can be separate and connected thereto. Typically, the entire bristle base member will be made of a plastic, such as polypropylene or polyester. In the embodiment shown, the thickness of the paddles is approximately 2-5 mm, with 4 mm being preferred.

Figure 4A:
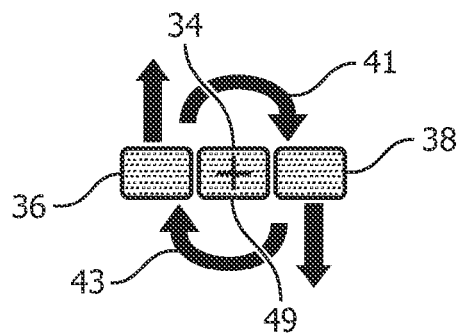
FIGS. 4A-4D are lateral cross-sectional views of the bristle base portion of FIG. 3, showing the relative motion of the bristle base during operation of the toothbrush.
Figure 4B:
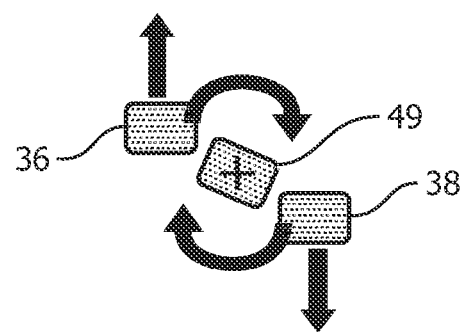
Figure 4C:
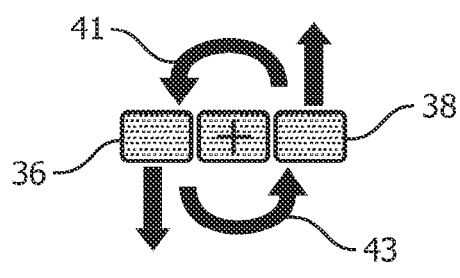
Figure 4D:
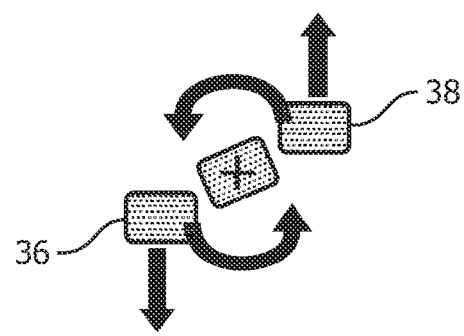

In operation, which is a key aspect of the invention, as the driveshaft 26 sweeps or rotates through a specified angle about axis 49, as shown in FIGS. 4A-4D, the two side paddle members 36, 38 move in and out alternately, toward and away from the teeth, while the central portion 34 rotates, as shown by arrows 41, 43. The bristles are not shown in FIGS. 4A-4D for clarity. FIGS. 4A, 4B show the rotation in one direction, while FIGS. 4C, 4D show the rotation in the opposing direction. Thus, relative to the teeth, the central portion 34 with bristles thereon produces a scrubbing action along the teeth surfaces, while the two paddle members produce an in-and-out, i.e. poking, motion relative to the teeth, which is particularly effective for the interproximal areas between the teeth. Hence, a dual motion brushhead is achieved without any mechanical linkages, due to the cantilever arrangement of the two paddle members and a sweeping, i.e. partially rotating, action of the appliance driveshaft, which drives the central portion of the brushhead in a scrubbing-type action on the teeth, but also produces the in and out action of the paddle members. As indicated above, the multi-motion requires that the brushhead be driven rotationally in a side-to-side (oscillating) manner about the axis of the neck portion. An appliance motor, driven by a sinusoidal signal, produces the required driveshaft motion for the brushhead. For sweeping motion toothbrushes, with a frequency in the range of 150-300 Hz, the in-and-out action of the two paddle members will have the same frequency. The amplitude of the paddle member motion is a function of paddle stiffness, paddle mass and loading of the brushhead by user action. The paddle stiffness is a function of the geometry of the paddle, described above, and the modulus of elasticity of the brushhead material.

Accordingly, an effective multi-motion toothbrush is desirably achieved having two important cleansing actions, produced by the arrangement and configuration of the bristle base assembly itself without any additional mechanical cams or linkages.

The bristle base arrangement can also be used for just in-and-out (toward and away from the teeth) single motion action. The structural arrangement of the brushhead is shown in FIG. 5 at 52. It includes two substantially identical paddle members 54 and 56 (except for the curved free ends) which are substantially co-planar. The physical dimensions of the paddle members, the rotation of the driveshaft and the range of the poking motion is similar to that of the embodiment of FIG. 3. The space between the two paddle members in this case is approximately 0.5-1 mm.

Figure 6A:
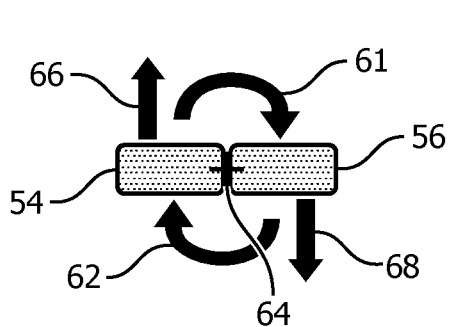
FIGS. 6A-6D are lateral cross-sectional views of the bristle base of FIG. 5, showing the relative motion of the bristle base portion during operation of the toothbrush.
Figure 6B:
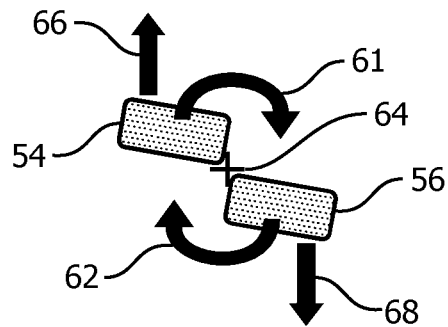
Figure 6C:
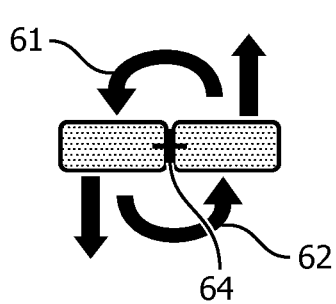
Figure 6D:
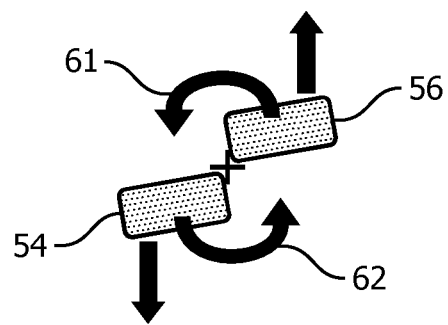

As shown in FIGS. 6A-6D, as the driveshaft 26 sweeps through a specific angle, as shown by arrows 61 and 62 about axis 64, the two paddle members 54, 56 alternately move toward and away from the teeth, as shown by arrows 66, 68. FIGS. 6A, 6B show the movement of paddle members 54, 56 when the driveshaft rotates in one direction, while FIGS. 6C and 6D show the movement of paddle members 54, 56 when the driveshaft rotates in the other direction. With bristles attached to the paddle members, a poking (in/out) motion is produced, which again is particularly effective for interproximal cleaning Accordingly, a new brushhead for a power toothbrush has been disclosed which is arranged and configured to produce a multi-motion action by virtue of the bristle base structure and arrangement, when the brushhead structure is driven in a sweeping (partially rotating) motion, without any mechanical linkages or cams.

Although a preferred embodiment of the invention has been disclosed for purposes of illustration, it should be understood that various changes, modifications and substitutions may be incorporated in the embodiment without departing from the spirit of the invention, which is defined by the claims which follow.

The invention claimed is:

1. A power toothbrush having a back-and-forth sweeping-type driving motion produced by a drive assembly, comprising:
a handle portion (14) including a drive assembly (16), wherein the drive assembly includes a driveshaft (26) configured to produce a back-and-forth, partially rotating, motion; and
a brushhead assembly (12) comprising:
a neck portion (30) configured for attachment to an extending driveshaft portion (26) of the drive assembly; and
a bristle base member (35) positioned at a distal end of the neck portion, the bristle base member including a central portion (34) and two paddle members (36,38) on opposing sides of the central portion, the central portion and the paddle members extending at proximal ends in cantilever fashion, respectively, from the distal end of the neck portion, wherein distal ends of the central portion and the paddle members are free to move, the central portion being configured and arranged to be driven by the drive assembly and follow the movement of the drive assembly in a back-and-forth sweeping, partially rotating, motion for cleansing action along the teeth, and the two paddle members being configured and arranged to move in and out, toward and away from the teeth when the central portion is cleansing the teeth.

2. The power toothbrush of claim 1, wherein the paddle members are each approximately 12-36 mm long, 2-5 mm wide and 2 -5 mm thick.

3. The power toothbrush of claim 2, wherein the paddle members are approximately 4 mm thick.

4. The power toothbrush of claim 1, wherein the sweeping motion of the drive assembly covers 5-20° and wherein the in-and-out motion is for 0.5 mm-5 mm.

5. The power toothbrush of claim 4, wherein the sweeping motion is preferably in the range of 7-14° and the in-and-out motion is approximately 2 mm.

6. The power toothbrush of claim 1, wherein the two paddle members are substantially identical and co-planar with the central portion, and wherein the central portion includes an end section at its distal end, the end section extending slightly beyond the opposing ends of the paddle members and covers substantially the entire width of the bristle base member.

\* \* \* \* \*